US012702651B2

(12) United States Patent
Karolchyk et al.

(10) Patent No.: US 12,702,651 B2
(45) Date of Patent: Aug. 11, 2026

(54) EPINEPHRINE-BASED OPHTHALMIC COMPOSITIONS FOR INTRAOCULAR ADMINISTRATION AND METHODS FOR FABRICATING THEREOF

(71) Applicant: Harrow IP, LLC, Nashville, TN (US)

(72) Inventors: John Scott Karolchyk, Lake Hopatcong, NJ (US); Mark L. Baum, San Diego, CA (US); Dennis Saadeh, Nashville, TN (US)

(73) Assignee: Harrow IP, LLC, Nashville, TN (US)

( * ) Notice: Subject to any disclaimer, the term of this patent is extended or adjusted under 35 U.S.C. 154(b) by 1093 days.

(21) Appl. No.: 17/384,373

(22) Filed: Jul. 23, 2021

(65) Prior Publication Data

US 2021/0346318 A1 Nov. 11, 2021

Related U.S. Application Data

(63) Continuation-in-part of application No. 17/330,023, filed on May 25, 2021, now abandoned, which is a continuation of application No. 15/247,524, filed on Aug. 25, 2016, now Pat. No. 11,045,432, which is a continuation-in-part of application No. 14/506,120, filed on Oct. 3, 2014, now Pat. No. 10,993,921.

(60) Provisional application No. 61/947,778, filed on Mar. 4, 2014, provisional application No. 61/892,872, filed on Oct. 18, 2013, provisional application No. 61/886,269, filed on Oct. 3, 2013.

(51) Int. Cl.

| | |
|---|---|
| ***A61K 31/137*** | (2006.01) |
| ***A61K 9/00*** | (2006.01) |
| ***A61K 9/19*** | (2006.01) |
| ***A61K 31/19*** | (2006.01) |
| ***A61K 31/4409*** | (2006.01) |
| ***A61K 45/06*** | (2006.01) |
| ***A61K 47/02*** | (2006.01) |
| ***A61K 47/16*** | (2006.01) |
| ***A61K 47/18*** | (2017.01) |
| ***B65D 25/04*** | (2006.01) |

(52) U.S. Cl.

CPC .......... *A61K 31/137* (2013.01); *A61K 9/0019* (2013.01); *A61K 9/0048* (2013.01); *A61K 9/0051* (2013.01); *A61K 9/19* (2013.01); *A61K 31/19* (2013.01); *A61K 31/4409* (2013.01); *A61K 45/06* (2013.01); *A61K 47/02* (2013.01); *A61K 47/16* (2013.01); *A61K 47/183* (2013.01); *B65D 25/04* (2013.01)

(58) Field of Classification Search

CPC ... A61K 31/137; A61K 31/167; A61K 31/198

See application file for complete search history.

(56) References Cited

U.S. PATENT DOCUMENTS

| | | | |
|---|---|---|---|
| 3,808,317 | A | 4/1974 | Hecht et al. |
| 4,525,346 | A | 6/1985 | Stark |
| 4,550,022 | A | 10/1985 | Garabedian et al. |
| 4,590,210 | A | 5/1986 | Langham |
| 5,654,337 | A | 8/1997 | Roentsch et al. |
| 5,709,852 | A | 1/1998 | Gopalkrishnan et al. |
| 6,562,002 | B1 | 5/2003 | Taylor |
| 9,301,936 | B2 | 4/2016 | Buderer et al. |
| 10,285,957 | B2 | 5/2019 | Karolchyk |
| 10,993,921 | B2 | 5/2021 | Karolchyk et al. |
| 2002/0146375 | A1 | 10/2002 | Schreiber et al. |
| 2003/0216413 | A1 | 11/2003 | Root-Bernstein et al. |
| 2004/0072809 | A1 | 4/2004 | Demopulos et al. |
| 2004/0076588 | A1 | 4/2004 | Batycky et al. |
| 2005/0074414 | A1 | 4/2005 | Tamarkin et al. |
| 2005/0118231 | A1 | 6/2005 | El Meski |
| 2005/0176823 | A1 | 8/2005 | Diaz |
| 2007/0060877 | A1 | 3/2007 | Bassarab |
| 2007/0196324 | A1 | 8/2007 | Keefe et al. |
| 2008/0269347 | A1 | 10/2008 | Bruss |
| 2009/0017120 | A1 | 1/2009 | Trimble et al. |
| 2010/0311705 | A1 | 12/2010 | Demopulos |
| 2011/0237681 | A1 | 9/2011 | Batycky et al. |
| 2012/0129944 | A1 | 5/2012 | Baillie et al. |
| 2012/0220637 | A1* | 8/2012 | Khatib .................... A61P 17/00 514/357 |
| 2013/0210840 | A1 | 8/2013 | Grasela et al. |
| 2014/0235691 | A1* | 8/2014 | Demopulos .......... A61K 31/407 514/413 |
| 2015/0017151 | A1 | 1/2015 | Buderer |
| 2015/0119440 | A1 | 4/2015 | Karolchyk et al. |
| 2016/0354308 | A1 | 12/2016 | Karolchyk et al. |

FOREIGN PATENT DOCUMENTS

| | | | |
|---|---|---|---|
| CA | 2002643 | A1 | 5/1990 |
| EP | 2246045 | A1 | 11/2010 |
| FR | 2779061 | A1 | 12/1999 |

(Continued)

OTHER PUBLICATIONS

West (Journal of Pharmacy and Pharmacology vol. 12 pp. 113T-115T published 1960), (Year: 1960).*

AK-Dilate 2.5% phenylephrine hydrochloride ophthalmic solution Product page from Falcon Pharmaceuticals and Alcon Laboratories (Year: 2014).*

AK-Dilate from Falcon Pharmaceuticals and Alcon Laboratories (Year: 2012).*

Saettone (J. Pharm. Pharmacol. vol. 32 pp. 519-521 published 1980) (Year: 1980).*

AK-Dilate product page (Year: 2014).*

(Continued)

*Primary Examiner* — George W Kosturko

(74) *Attorney, Agent, or Firm* — Polsinelli PC

(57) ABSTRACT

Pharmaceutical compositions for intraocular injection are described, the compositions comprise therapeutically effective quantity of lyophilized preservative-free and sulfite-free epinephrine or adrenaline and a metal chelator. Methods for fabricating the compositions and using them for intraocular injections are also described.

16 Claims, 3 Drawing Sheets

(56) References Cited

FOREIGN PATENT DOCUMENTS

| | | | | |
|---|---|---|---|---|
| JP | 07-502544 A | | 3/1995 | |
| JP | 2004-509920 A | | 4/2004 | |
| JP | 2006-504661 A | | 2/2006 | |
| JP | 2016-532723 A | | 10/2016 | |
| WO | 1994/008602 A1 | | 4/1994 | |
| WO | 1998/03641 A1 | | 1/1998 | |
| WO | 2002/026223 A2 | | 4/2002 | |
| WO | 2004/010894 A2 | | 2/2004 | |
| WO | WO-2007122580 A2 | * | 11/2007 | ........... A61K 31/137 |
| WO | 2009/111083 A2 | | 9/2009 | |
| WO | 2010/057007 A1 | | 5/2010 | |

OTHER PUBLICATIONS

Dubois (BMC Ophthalmology vol. 6 Issue 36 pp. 1-4, published 2006). (Year: 2006).*

West, G.B., Journal of Pharmacy and Pharmacology, vol. 12, p. 113T-115T, Published 1960.

Das Gupta, V., J. Clin. Hop Pharm, vol. 11, pp. 449-452, 1986.

Slack, American Journal of Ophthalmology, vol. 110, p. 77-82, 1990.

Shugar et al., "Use of epinephrine for IFIS prophylaxis," Journal of Cataract & Refractive Surgery, 2006, 32(7):1074-1075.

Sinnott et al., "On the mechanism by which epinephrine potentiates lidocaine's peripheral nerve block," The Journal of American Society of Anesthesiologists, 2003, 98(1):181-188.

International Search Report with Written Opinion corresponding to International Patent Application No. PCT/US2014/059077, dated Jan. 26, 2015.

Overgaard, "How to Make Sterile Water and Sterile Saline," Phoenix Children's Hospital, 2006.

Non-FInal Rejection corresponding to U.S. Appl. No. 14/506,120, dated Oct. 5, 2017, 28 pages.

Shugar, J.K., "Intracameral Epinephrine for IFIS Prophylaxis," Cataract & Refractive Surgery Today, 2006, pp. 1-13.

BSS Product Page, Alcon Laboratories, Inc., 2012.

Verhoff, F. et al., Ulmann's Encyclopedia of Industrial Chemistry: Citric Acid, Wiley-VCH GMBH & Co. KGaA, Weinheim, pp. 1-9, 2015.

Schulze Jr., Richard, "EPI-Shugarcaine With Plain Balanced Salt Solution for Prophylaxis of Intraoperative Floppy-Iris Syndrome," Journal of Cataract Surgery, 2010, 35:523.

Stewart, R., et al., "Efficacy and safety profile of ketorolac 0.5% ophthalmic solution in the prevention of surgically induced miosis during cataract surgery," Clinical Therapeutics, 1999, 21:723-732.

Grubstein, B., et al., "Stabilization of Epinephrine local anesthetic injectable solution using reduced levels of Sodium Metabisulfite and EDTA" Drug Development and Industrial Pharmacy, 1992, 18:1549-1566.

PH, Encyclopedia Brittanica, published online, 1998, https://britannica.com/science/pH.

Zhang, et al., "Study of mixed micelles and interaction parameters for polymeric nonionic and normal surfactants," Journal of Nanoscience and Nanotechnology, 2006.

United States Pharmacopoeia 21st Review, National Formulary 16th Review, 1985, pp. 1651, 592-596, 1662, 571-572, 827-830, 883-884.

PCT/US2014/059077, filed Oct. 3, 2014, John Scott Karolchyk.

U.S. Appl. No. 15/241,958, filed Aug. 19, 2016, John Scott Karolchyk.

U.S. Appl. No. 14/506,120, filed Oct. 3, 2014, John Scott Karolchyk.

Remington, The Science and Practice of Pharmacy, 21st Edition, 2005, pp. 828-829.

American Reagent Laboratories, Inc., MSDS of Epinephrine Injection from Lutipold Pharmaceuticals, 1998, 4 pages.

Lorenzetti, "Dose-dependent Influence of Topically Instilled Adrenergic Agents on Intraocular Pressure and Outflow Facility in the Rabbit", Exp Eye Res, 1971, 12:80-87.

Roscoe et al., "Chelating Agents as Color Stabilizers for Epinephrine Hydrochloride Solutions", Journal of American Pharmaceutical Association, 1956, 45(7): 464-470.

Office Action in U.S. Appl. No. 17/330,023 dated Feb. 1, 2023, 19 pages.

Lorente, et al. "Intracameral Phenylephrine 1.5% for Prophylaxis against Intraoperative Floppy Iris Syndrome: Prospective, Randomized Fellow Eye Study", Ophthalmology 2012; 119:2053-2058.

* cited by examiner

EPINEPHRINE-BASED OPHTHALMIC COMPOSITIONS FOR INTRAOCULAR ADMINISTRATION AND METHODS FOR FABRICATING THEREOF

FIELD OF THE INVENTION

This application is a continuation-in-part-application of U.S. patent application Ser. No. 15/247,524 filed on Aug. 25, 2016, entitled "Epinephrine-Based Compositions and Methods of Fabricating Thereof," the entire contents of which are hereby incorporated by reference, which is a continuation-part-application of U.S. patent application Ser. No. 14/506,120 filed on Oct. 3, 2014 entitled "Epinephrine-Based Compositions and Methods for Fabricating Thereof," the entire contents of which is hereby incorporated by reference, and to which it claims priority under 35 U.S.C. § 120, and which claims priority under 35 U.S.C. § 119(e) to each of the following U.S. Provisional Applications: No. 61/886,269 filed on Oct. 3, 2013 entitled "Epinephrine Compositions for Intraocular Administration and Methods for Fabricating Thereof," No. 61/892,872 filed on Oct. 18, 2013 entitled "Epinephrine-Based Compositions and Methods for Fabricating Thereof," and No. 61/947,778 filed on Mar. 4, 2014 entitled "Epinephrine Compositions for Intraocular Administration and Methods for Fabricating Thereof," the entire contents of each of which is hereby incorporated by reference.

The present invention relates generally to the field of ophthalmology and more specifically to injectable ophthalmological compositions comprising epinephrine, phenylephrine, and tropicamide, and to methods of preparing such compositions.

BACKGROUND

Epinephrine (EPI or epi) is a drug that is frequently used in ophthalmological treatments, procedures and surgeries, e.g., cataract surgery or glaucoma surgery. Epinephrine is known to be used for such purposes either alone or as an active ingredient in a composition, e.g., in intracameral epi-Shugarcaine for intraoperative floppy iris syndrome (IFIS) and pupil dilation. Epinephrine is a perishable product with limited shelf life and limited stability. Epinephrine quite easily gets oxidized to form adrenochrome (chemically, catecholamine quinone). The oxidation causes deactivation of epinephrine and the concomitant loss of its valuable medicinal properties. Therefore, most commercially available epinephrine contains preservatives and stabilizers, typically bisulfites, for a prolonged shelf life and stability.

However, using epinephrine with preservatives is undesirable as it can cause toxicity in the eye, putting patients at risk for toxic anterior segment syndrome (TASS), an acute inflammation of the anterior segment. Although most TASS cases are cured with topical steroids, severe cases can lead to cornea transplantation and iris atrophy. Having alternative non-toxic epinephrine-based compositions and procedures utilizing them that are safer but equally effective is, therefore, desirable.

This disclosure provides an alternative procedure that includes an intraocular injection that employs preservative- and sulfite-free compositions of epinephrine or essentially preservative- and sulfite-free compositions of the same. Such alternative procedure can achieve patient outcomes that are as good as, or better than, the current regimen, removing the issues of toxicity. This patent application discloses epinephrine-based pharmaceutical compositions suitable for intraocular injections that can achieve such positive patient outcomes, and methods of fabricating and administering the same.

SUMMARY

Figure 1:
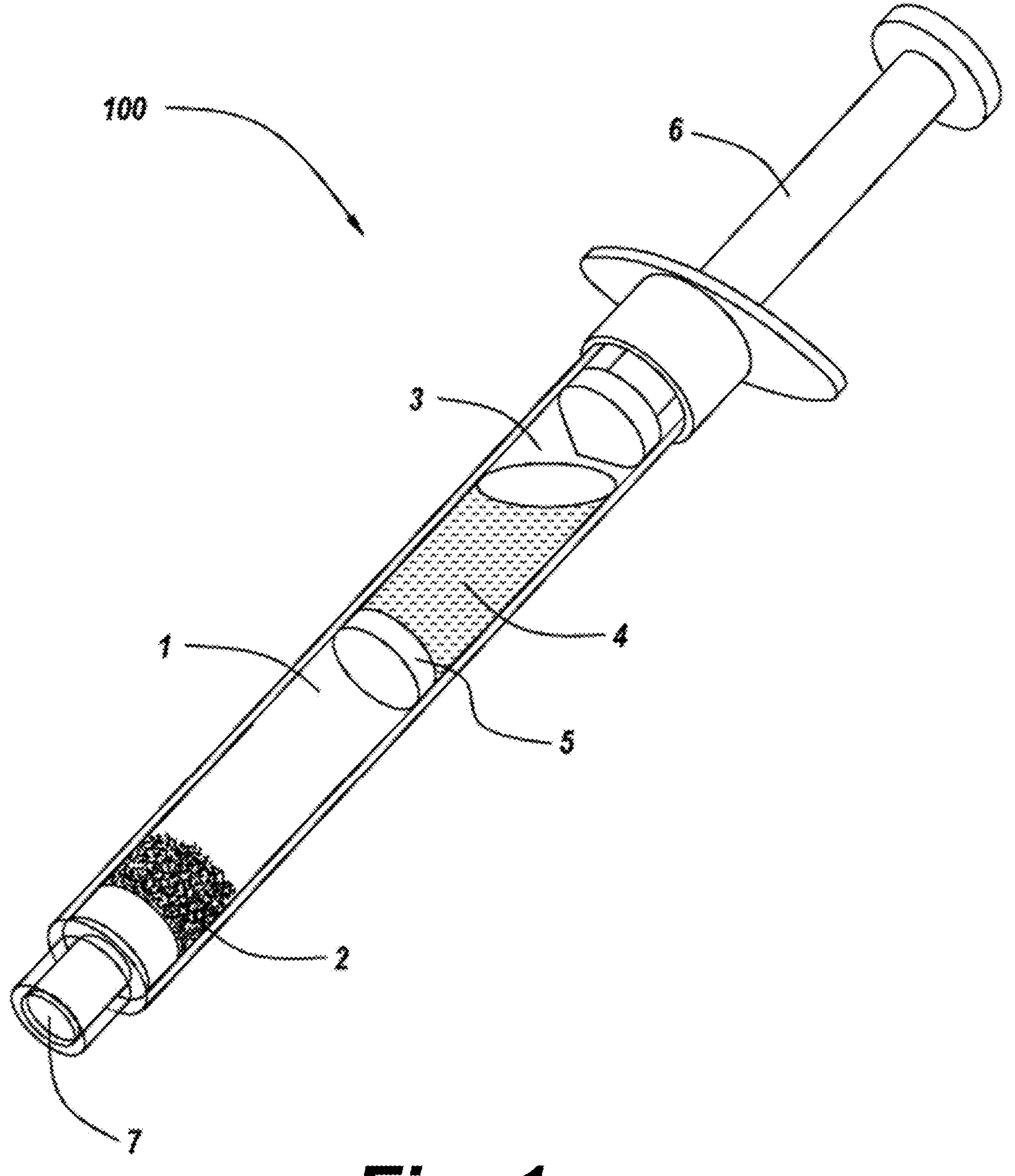
FIG. 1 shows schematically one kind of a bicameral container in which a method of for preparing a pharmaceutical composition can be carried out according to one embodiment of the invention.

According to one embodiment of the invention, pharmaceutical composition(s) for intraocular injection is (are) provided, the composition(s) comprising a therapeutically effective quantity of lyophilized epinephrine and/or phenylephrine, the pharmaceutical composition(s) being free of sulfites and is free of preservatives, or being essentially free of sulfites and being essentially free of preservatives, or being free of sulfites and being essentially free of preservatives, or being essentially free of sulfites and being free of preservatives.

According to another embodiment of the invention, pharmaceutical composition(s) for intraocular injection is (are) provided, the composition(s) comprising a therapeutically effective quantity of lyophilized epinephrine and/or phenylephrine, and at least one metal chelator such as, e.g., ethylenediaminetetraacetic acid or acetylcysteine and pharmaceutically acceptable salts thereof.

According to yet another embodiment of the invention, a method for preparing a pharmaceutical composition for intraocular injection is provided, the method comprising lyophilizing the aqueous composition comprising a therapeutically effective quantity of epinephrine and/or phenylephrine that is free or essentially free of sulfites and is free or essentially free of preservatives and reconstituting the composition immediately prior to the use thereof, to obtain thereby the pharmaceutical composition for intraocular injection.

According to yet another embodiment of the invention, lyophilized epinephrine and/or phenylephrine-containing composition(s) described herein may further optionally include therapeutically effective quantity (or quantities) of one or several other compounds such as anesthetic(s) (e.g., lidocaine) and/or non-steroid anti-inflammatory drugs (NSAID) such as ketorolac.

DETAILED DESCRIPTION

A. Terms, Definitions and Abbreviations

Unless specific definitions are provided, the nomenclatures utilized in connection with, and the laboratory procedures and techniques of analytical chemistry, synthetic organic and inorganic chemistry described herein, are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, formulating compositions and testing them. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. The section headings used herein are for organizational purposes only and are not to be construed as limiting the subject matter described.

As used herein, "or" means "and/or" unless stated otherwise. Furthermore, use of the term "including" as well as other forms, such as "includes," and "included," is not limiting.

"About" as used herein means that a number referred to as "about" comprises the recited number plus or minus 1-10% of that recited number. For example, "about" 100 degrees can mean 95-105 degrees or as few as 99-101 degrees depending on the context. Whenever it appears herein, a numerical range such as "1 to 20" refers to each integer in the given range; i.e., meaning only 1, only 2, only 3, etc., up to and including only 20.

The term "pharmaceutical composition" is defined as a chemical or biological compound or substance, or a mixture or combination of two or more such compounds or substances, intended for use in the medical diagnosis, cure, treatment, or prevention of disease or pathology.

The term "intraocular injection" refers to an injection that is administered by entering the eyeball of the patient.

The term "preservative" for the purposes of the present invention refers to a chemical substance that is added to a pharmaceutical composition to prevent the pharmaceutical composition from deterioration, decomposition or degradation or to substantially reduce or decelerate the degree and/or the speed of such deterioration, decomposition or degradation.

Accordingly "preservative-free" means a pharmaceutical composition that does not include a preservative or includes not more than a trace amount of a preservative. Thus, the pharmaceutical composition can be substantially free of preservative or alternatively include not more than a trace amount of a preservative. It is explicitly understood that for the purposes of the present application, metal chelators such as EDTA defined below are not considered preservatives. Accordingly, compositions that comprise metal chelators such as EDTA are considered preservative-free if they include no other preservative(s).

Trace amounts of preservatives can include relatively low concentrations or amounts of preservatives in a pharmaceutical composition. In certain embodiments, relatively low concentrations of preservatives include concentrations of about 1 μM or less, or about 1% of the pharmaceutical composition by weight or less or about 1 μg per dosage unit of pharmaceutical composition or less.

In other embodiments, relatively low concentrations of preservatives include concentrations of about 100 nM or less, about 10 nM or less, about 1 nM or less, about 100 pM or less, about 10 pM or less or about 1 pM or less; or about 0.1% or less, or about 0.01% or less, or about 0.001% or less or about 0.0001% or less, each of the pharmaceutical composition by weight.

In other embodiments, relatively low amounts of preservatives in pharmaceutical compositions include pharmaceutical compositions wherein preservatives are provided at about 100 ng or less, about 10 ng or less, about 1 ng or less, about 100 pg or less, about 10 pg or less or about 1 pg or less, each per dosage unit of pharmaceutical composition.

The term "anti-oxidant" for the purposes of the present invention refers to a chemical substance that is added to a pharmaceutical composition to prevent or inhibits the oxidation of molecules that are present in the active component of the composition, such as epinephrine. It is explicitly understood that for the purposes of the present application, anti-oxidants are not considered preservatives. Accordingly, compositions that optionally comprise anti-oxidants as described below are considered preservative-free if they include no other preservative(s).

The term "sulfite" refers to compounds that comprise the sulfite ion $50_3^{2-}$ such as normal salts of sulfurous acid $H_2S0_3$. For the purposes of the present application, the term "sulfite" is also inclusive of bisulfites, i.e., compounds that comprise the bisulfate ion $HS0_3^-$ such as acid salts of sulfurous acid.

Accordingly "sulfite-free" means a pharmaceutical composition that does not include a sulfite or includes a relatively low concentration or amount of a sulfite. Thus, the pharmaceutical composition can be substantially free of sulfite or have not more than a trace amount of sulfite. It is explicitly understood that for the purposes of the present application, metal chelators such as EDTA defined below are not considered sulfites. Accordingly, compositions that comprise metal chelators such as EDTA are considered sulfite-free if they include no other sulfite(s).

Trace amounts of sulfites can include relatively low concentrations or amounts of sulfites in a pharmaceutical composition. Relatively low concentrations of sulfites include concentrations include concentrations of about 1 μM or less, or about 1% of the pharmaceutical composition by weight or less or about 1 μg per dosage unit of pharmaceutical composition or less.

In other embodiments, relatively low concentrations of sulfites include concentrations of about 100 nM or less, about 10 nM or less, about 1 nM or less, about 100 pM or less, about 10 pM or less or about 1 pM or less; or about 0.1% or less, or about 0.01% or less, or about 0.001% or less or about 0.0001% or less, each of the pharmaceutical composition by weight.

In other embodiments, relatively low amounts of sulfites in pharmaceutical compositions include pharmaceutical compositions wherein preservatives are provided at about 100 ng or less, about 10 ng or less, about 1 ng or less, about 100 pg or less, about 10 pg or less or about 1 pg or less, each per dosage unit of pharmaceutical composition.

The terms "lyophilize" and "lyophilized" refer to the process of freeze-drying (a dehydration process that includes freezing the material and then reducing the pressure to allow the frozen water in the material to sublimate) and to the products of this process.

The term "partially lyophilized" refers to compositions that comprise both a lyophilized portion of a product and a non-lyophilized portion of the same.

The term "epinephrine" which is synonymous with "adrenaline" (the two terms may be used interchangeably) refers to any stereoisomer of 4-(1-hydroxy-2-(methylamino) ethyl) benzene-1,2-diol, a chemical compound having the following chemical structure (the R-stereoisomer is shown):

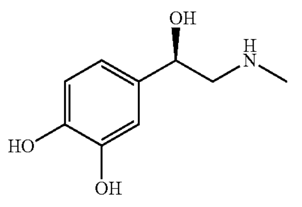

The term “phenylephrine” refers to any stereoisomer of 3-[1-hydroxy-(methylamino) ethyl]phenol, a chemical compound having the following chemical structure (also the R-stereoisomer is shown):

The term “EPI-Shugarcaine” refers to a composition consisting of about 25% (vol.) of

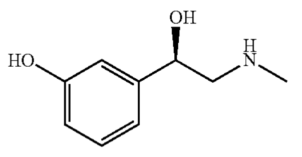

1:1,000 bisulfite-free aqueous solution of epinephrine, about 19% (vol.) of preservative-free lidocaine and the balance, BSS Plus® (balanced salt solution available from Alcon Laboratories of Fort Worth, Texas).

The term “anesthetic” refers to a substance that that causes loss of sensation and therefore induces insensitivity or low sensitivity to pain.

The term “lidocaine” refers to 2-diethylamino-N-(2,6-dimethylphenyl)acetamide, a chemical compound having the following chemical structure:

The abbreviation “EDTA” is 2-

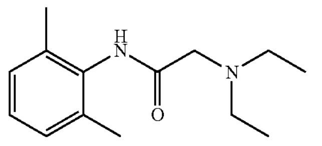 [SMILES: CCN(CC)CC(=O)Nc1c(C)cccc1C]

(12[bis(carboxymethyl)amino]ethyl}(carboxymethyl) amino) acetic acid (a chemical compound that is also known under several other names such as edetic acid or ethylenediaminetetraacetic), and its various protonated forms, EDTA having the following chemical structure:

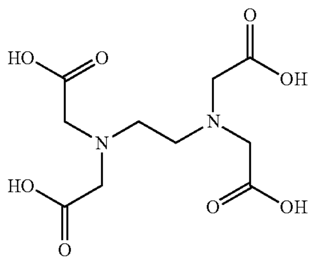 [SMILES: O=C(O)CN(CCN(CC(=O)O)CC(=O)O)CC(=O)O]

The terms “chelating agent” or “metal chelator” refer to a chemical compound that coordinates with a metal to form a chelate, which is a compound containing an organic ligand bonded to a central metal atom at two or more points.

The terms “non-steroid anti-inflammatory drugs” or “NSAID” refer to a class of compounds that are free of any steroid moieties yet are capable of providing analgesic, antipyretic and/or anti-inflammatory effects.

The term “ketorolac” refers to a chemical composition comprising, in the 1:1 mass ratio, 2-amino-2-(hydroxymethyl)-1,3-propanediol, a chemical compound having the chemical structure $NH_2$—C—$(CH_2OH)_3$ and 5-benzoyl-2,3-dihydro-1H-pyrrolizine-1-carboxylic acid, a chemical compound having the following chemical structure:

The term “salt” refers to an ionic compound which is a product of the neutralization reaction of an acid and a base.

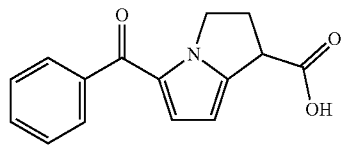 [SMILES: O=C(c1ccccc1)c1ccc2n1CCC2C(=O)O]

The term “phacoemulsification” refers to an ophthalmological surgical procedure in which the eye’s internal lens is ultrasonically emulsified and aspirated from the eye.

The term “carrier” refers to a substance that serves as a vehicle for improving the efficiency of delivery and the effectiveness of a pharmaceutical composition. One non-limiting example of a carrier for the purposes of the instant application is water such as de-ionized sterile water.

The term “therapeutically effective amount” is defined as the amount of the compound or pharmaceutical composition that will elicit the biological or medical response of a tissue, system, animal or human that is being sought by the researcher, medical doctor or other clinician.

The term “pharmaceutically acceptable” is defined as a carrier, whether diluent or excipient, that is compatible with the other ingredients of the formulation and not deleterious to the recipient thereof.

The terms “administration of a composition” or “administering a composition” is defined to include an act of providing a compound or pharmaceutical composition of the application to the subject in need of treatment.

The term “rapid” as it relates to the rate of dilation of a subject’s pupil is defined herein as less than one minute. Therefore, rapid dilation of a subject’s pupil is dilation that occurs in less than one minute.

B. Embodiments

Intracameral epinephrine is commonly used off-label to dilate and stabilize the pupil intraoperatively by preventing intraoperative floppy iris syndrome. However, as mentioned above, commonly available epinephrine is frequently quite toxic. Those having ordinary skill in the art believe that the toxicity is caused by the high buffer capacity of the bisulfate that is present in the epinephrine solution rather than by the epinephrine itself. It is, therefore, desirable to only use for direct intracameral injection preservative-free preparations of epinephrine that are also bisulfite-free. Another potential problem with undiluted epinephrine taken directly from the vial is that it has a low pH of approximately 3.0, which is well outside the 6.0 to 8.0 pH range thought by those having ordinary skill in the art to be safe for the corneal endothelium.

In view of the foregoing, embodiments described in the present application are directed to pharmaceutical compositions for intraocular injections that are free of the above-mentioned problems, drawbacks and defects. The compositions are preservative-free and sulfite-free and include an active component comprising, consisting essentially of, or consisting of a therapeutically effective quantity of epinephrine or adrenaline or pharmaceutically acceptable salts thereof (e.g., a hydrochloride) and a pharmaceutically acceptable carrier therefor. Bisulfite-free epinephrine is available from American Regent Laboratories of Shirley, New York.

In addition to epinephrine, the active component may optionally include other compounds, non-limiting examples of which include phenylephrine, EPI-Shugarcaine and/or tropicamide. Some anti-oxidants may be also optionally used, if desired, as a part of the active component, i.e., in combination with epinephrine, to provide some additional stability to epinephrine. Non-limiting examples of acceptable anti-oxidants that may be so used include ascorbic acid, vitamin E, glutathione and acetylcysteine. It has to be kept in mind that these additional anti-oxidants typically provide only limited stability to epinephrine, usually up to 60 days, when the composition is kept refrigerated.

In some embodiments, the composition of the present disclosure may include phenylephrine hydrochloride. In some additional embodiments, the phenylephrine hydrochloride may have a concentration in the composition of between about 0.02% (w/v) to about 1.5% (w/v). In some aspects, the phenylephrine hydrochloride may have a concentration in the composition of between about 0.1% (w/v) to about 1.4% (w/v), about 0.3% (w/v) to about 1.3% (w/v), about 0.5% (w/v) to about 1.2% (w/v), about 0.7% (w/v) to about 1.1% (w/v), or about 0.9% (w/v) to about 1% (w/v). In some additional aspects, the phenylephrine hydrochloride may have a concentration in the composition of between about 0.02% (w/v) to about 0.1% (w/v), about 0.1% (w/v) to about 0.2% (w/v), about 0.2% (w/v) to about 0.3% (w/v), about 0.3% (w/v) to about 0.4% (w/v), about 0.4% (w/v) to about 0.5% (w/v), about 0.5% (w/v) to about 0.6% (w/v), about 0.6% (w/v) to about 0.7% (w/v), about 0.7% (w/v) to about 0.8% (w/v), about 0.8% (w/v) to about 0.9% (w/v), about 0.9% (w/v) to about 1% (w/v), about 1% (w/v) to about 1.1% (w/v), about 1.1% (w/v) to about 1.2% (w/v), about 1.2% (w/v) to about 1.3% (w/v), about 1.3% (w/v) to about 1.4% (w/v), or about 1.4% (w/v) to about 1.5% (w/v). In still further aspects, the phenylephrine hydrochloride may have a concentration of about 0.02% (w/v), 0.1% (w/v), 0.2% (w/v), 0.3% (w/v), 0.4% (w/v), 0.5% (w/v), 0.6% (w/v), 0.7% (w/v), 0.8% (w/v), 0.9% (w/v), 1% (w/v), 1.1% (w/v), 1.2% (w/v), 1.3% (w/v), 1.4% (w/v), or about 1.5% (w/v). In one example, the phenylephrine hydrochloride has a concentration of about 1% (w/v).

In some embodiments, the composition of the present disclosure may include tropicamide. In some embodiments, the tropicamide may have a concentration in the composition of between about 0.02% (w/v) to about 0.1% (w/v). In some aspects, the tropicamide may have a concentration in the composition of between about 0.03% (w/v) to about 0.08% (w/v) or about 0.04% (w/v) to about 0.06% (w/v). In some additional aspects, the tropicamide may have a concentration in the composition of between about 0.02% (w/v) to about 0.03% (w/v), about 0.03% (w/v) to about 0.04% (w/v), about 0.04% (w/v) to about 0.05% (w/v), about 0.05% (w/v) to about 0.06% (w/v), about 0.06% (w/v) to about 0.07% (w/v), about 0.07% (w/v) to about 0.08% (w/v), about 0.08% (w/v) to about 0.09% (w/v), or about 0.09% (w/v) to about 0.1% (w/v). In still further aspects, the tropicamide may have a concentration in the composition of about 0.02% (w/v), 0.03% (w/v), 0.04% (w/v), 0.05% (w/v), 0.06% (w/v), 0.07% (w/v), 0.08% (w/v), 0.09% (w/v), or about 0.1% (w/v). In one example, the tropicamide has a concentration of about 0.05% (w/v).

In some further embodiments, the active component may optionally include still other compounds, such as one or several anesthetics (e.g., lidocaine) and/or one or several non-steroid anti-inflammatory drug(s). Non-limiting examples of alternative acceptable anesthetics that may be used in any combination with, or instead of, lidocaine, include proparacaine, procaine, tetracaine and combinations thereof. Non-limiting examples of acceptable NSAID's that can be so utilized include ketorolac, ketoprofen, flurbiprofen, bromfenac, diclofenac and combinations thereof.

In some embodiments, the anesthetic may have a concentration in the composition of between about 0.5% (w/v) to about 1.5% (w/v). In some aspects, the anesthetic may have a concentration in the composition of between about 0.6% (w/v) to about 1.4% (w/v), about 0.7% (w/v) to about 1.3% (w/v), about 0.8% (w/v) to about 1.2% (w/v), or about 0.9% (w/v) to about 1.1% (w/v). In some additional aspects, the anesthetic may have a concentration in the composition of between about 0.5% (w/v) to about 0.6% (w/v), about 0.6% (w/v) to about 0.7% (w/v), about 0.7% (w/v) to about 0.8% (w/v), about 0.8% (w/v) to about 0.9% (w/v), about 0.9% (w/v) to about 1% (w/v), about 1% (w/v) to about 1.1% (w/v), about 1.1% (w/v) to about 1.2% (w/v), about 1.2% (w/v) to about 1.3% (w/v), about 1.3% (w/v) to about 1.4% (w/v), or about 1.4% (w/v) to about 1.5% (w/v). In still further aspects, the anesthetic may have a concentration in the composition of about 0.5% (w/v), 0.6% (w/v), 0.7% (w/v), 0.8% (w/v), 0.9% (w/v), 1% (w/v), 1.1% (w/v), 1.2% (w/v), 1.3% (w/v), 1.4% (w/v), or about 1.5% (w/v). In one example, the anesthetic is lidocaine and has a concentration in the composition of about 1% (w/v).

In some embodiments, the non-steroid anti-inflammatory drug may have a concentration in the composition of between about 0.04% (w/v) to about 0.5% (w/v). In some aspects, the non-steroid anti-inflammatory drug may have a concentration in the composition of between about 0.04% (w/v) to about 0.4% (w/v), about 0.04% (w/v) to about 0.3% (w/v), about 0.04% (w/v) to about 0.2% (w/v), or about 0.04% (w/v) to about 0.1% (w/v). In some additional aspects, the non-steroid anti-inflammatory drug may have a concentration in the composition of between about 0.04% (w/v) to about 0.1% (w/v), about 0.1% (w/v) to about 0.15% (w/v), about 0.15% (w/v) to about 0.2% (w/v), about 0.2% (w/v) to about 0.25% (w/v), about 0.25% (w/v) to about 0.3% (w/v), about 0.3% (w/v) to about 0.35% (w/v), about 0.35% (w/v) to about 0.4% (w/v), about 0.4% (w/v) to about 0.45% (w/v), or about 0.45% (w/v) to about 0.5% (w/v). In still further aspects, the non-steroid anti-inflammatory drug may have a concentration in the composition of about 0.04% (w/v), 0.05% (w/v), 0.06% (w/v), 0.07% (w/v), 0.08% (w/v), 0.09% (w/v), 0.1% (w/v), 0.15% (w/v), 0.2% (w/v), 0.25% (w/v), 0.3% (w/v), 0.35% (w/v), 0.4% (w/v), 0.45% (w/v), or about 0.5% (w/v). In one example, the non-steroid anti-inflammatory drug is diclofenac and has a concentration in the composition of about 0.05% (w/v).

In sum, embodiments of the invention envision preservative-free and sulfite-free compositions having an active component, which includes any combination of epinephrine, and/or phenylephrine and/or EPI-Shugarcaine, and in addition, optionally, any combination of anesthetic(s) and/or non-steroid anti-inflammatory drug(s). In other words, at least one of epinephrine, phenylephrine, EPI-Shugarcaine and tropicamide is to be present in the active component, while the presence of any other additional components mentioned above is optional.

The contents of the active component in the pharmaceutical compositions of the present application may be between about 0.001 and about 0.5 mass %, such as between about 0.01 and about 0.3 mass %, for example, between about 0.03 and about 0.1 mass %. The compositions described in the present application further include certain additives, but, as indicated above, are free of preservatives and are free of sulfites. If NSAID(s) are to be used, one having ordinary skill in the art may select a proper ratio between epinephrine, and/or phenylephrine and/or EPI-Shugarcaine and NSAID(s). In exemplary, non-limiting embodiments, the mass ratio between phenylephrine and ketorolac may be between about 10:1 and about 3:1, such as about 4:1. In other exemplary, non-limiting embodiments, the mass ratio between phenylephrine and diclofenac may be between about 1:20.

According to embodiments of the present invention, a pharmaceutical composition for intraocular injection further comprises a quantity of least one chelating agent such as a metal chelator. One non-limiting example of an acceptable chelating agent that may be used in combination with epinephrine is ethylenediaminetetraacetic acid (EDTA) or pharmaceutically acceptable salts thereof, which is both a chelator and a stabilizer. One salt of EDTA that can provide stabilization of epinephrine is EDTA disodium. Other salts of EDTA, non-limiting examples of which include EDTA calcium disodium and EDTA magnesium disodium, may be also used instead of, or in combination with, EDTA disodium.

The contents of the chelating agent in the pharmaceutical compositions of the present application may be (expressed as the chelating agent to epinephrine mass ratio) between about 4:1 and 1:4, for example, about 1:2 (i.e., about 0.5 mg of EDTA per 1 mg of epinephrine). Those having ordinary skill in the art may select a specific chelating agent based on the needs of a particular patient or on the desired properties of the final composition and may also adjust the concentration of the active component and/or of the chelating agent in the composition, if desired.

In addition to the active component(s), chelating agent(s), anesthetic(s) and/or non-steroid anti-inflammatory drug(s), the composition may optionally include other components such as additives, adjuvants, diluents, modifiers, excipients, etc., so long as the composition remains both preservative-free and sulfite-free within the meaning of "preservative" defined above. Some non-limiting examples of such optionally useful suitable additives, diluents, adjuvants, modifiers, or excipients include acetylcysteine (acetylcysteine which is capable of eliminating, or at least reducing the quantity of, free radicals, and of providing nourishment to the eye), glutathione, ascorbic acid, vitamin E, balanced salts solution, boric acid, Polysorbate-80, sodium hydroxide, hydrochloric acid, and other excipients known in the art. Additionally, a composition of the present disclosure may include at least one tonicity adjusting agent, such as a chloride salt selected from the group consisting of sodium chloride, magnesium chloride, and potassium chloride, and other tonicity adjusting agents known in the art.

A variety of suitable methods are envisioned that one having ordinary skill in the art may employ to prepare preservative-free and sulfite-free epinephrine-based pharmaceutical compositions for intraocular injection according to embodiments described in the instant application. According to one non-limiting embodiment, composition I can be prepared first. To prepare composition I, a quantity of an active ingredient such as epinephrine, a quantity of a metal chelator such as EDTA, optionally, a quantity of at least one anesthetic, optionally, a quantity of at least one non-steroid anti-inflammatory drug and, optionally, a quantity of an non-preservative additive such as sodium chloride NaCl (e.g., if isotonicity has to be adjusted), may be combined in a depyrogenated glass container. The mixture may be then dissolved in sterile de-ionized water to form a clear aqueous solution.

Each of the ingredients used to make composition I is to be used in pre-determined quantity so that the final pharmaceutical composition have a desired ratio between the ingredients and a desired concentration of each of them. Those having ordinary skill in the art can determine the desired ratios and concentrations. The pH of the solution may be adjusted to a pH level ranging from slightly acidic, e.g., about 6.0, to slightly basic, e.g., about 8.0. The process of lyophilization of composition I may then be conducted to obtain the lyophilized product, composition II.

To conduct the process of lyophilization, the solution may be optionally de-gassed followed by freezing at low temperatures (e.g., −70° C. or lower) for a period of time (e.g., at least 24 hours) to allow the solution to completely solidify and to form proper ice crystals. Then, the frozen composition is subjected to a vacuum of at least 30 mm Hg for a period of time (e.g., at least 24 hours). As a result of exposure to the vacuum, the water sublimates from the frozen solution (i.e., transitions from the solid to the gas phase bypassing the liquid phase) to form a completely dry, powder-like substance which is the lyophilized composition II. Accordingly, composition II is a completely lyophilized preservative-free and sulfite-free pharmaceutical composition containing the active ingredient (e.g., epinephrine), the metal chelator (e.g., EDTA) and, optionally, other ingredients discussed above, if such optional ingredients are used in preparing composition I. Not more than trace quantity of residual water would be typically contained in composition II after the process of lyophilization is complete.

Composition II, i.e., the lyophilized dry epinephrine-based composition that is preservative-free and sulfite-free prepared according to methods described herein has remained stable for several months and is expected to continue being stable for as long as two years. Stability can be evaluated by those having ordinary skill in the art according to one or more of various methods, e.g., by the retention of potency after storage for a period of time, by showing that no loss (or not more than negligible loss) of concentration of epinephrine has occurred during the period of storage, or by visual observations such as no change in color.

Next, the dry composition II is to be reconstituted immediately prior to its use, for example, 1 hr or less before the surgery, or 30 minutes or less. To reconstitute the composition, a quantity of sterile de-ionized water for injection is to be added to the dry composition and a clear solution can thus obtained. The concentration of the active component such as epinephrine that is desirable to have for the injection determines the quantity of water to be added to the dry composition, to be chosen by one having ordinary skill in the art. In one exemplary non-limiting embodiment, the final product to be injected contains about 1 mg/mL of epinephrine, i.e., is a 1:1,000 solution.

As is clear from the discussion above, the use of lyophilized and then reconstituted composition II is then typically envisioned according to embodiments of the instant application. However, in other embodiments that can be also practiced, composition I described above may be optionally used for re-constitution, with or without pure sterile de-ionized water for injection being added also. Thus, in such optional embodiments, the pharmaceutical composition comprises a fully lyophilized portion (i.e., composition II), a non-lyophilized portion (i.e., composition I) and, optionally, an extra quantity of pure sterile de-ionized water. Those having ordinary skill in the art can determine the quantities of the fully lyophilized and non-lyophilized portions and of water so as to achieve the desired ratios of the ingredients and their concentrations.

A variety of apparatuses can be used for reconstituting the composition. For example, water can be added to the dry composition in a single container such as a vial. Once a clear solution has been formed, it can be collected by a syringe and injected or it can be picked up by an eye dropper or a pipette and administered as drops, if desired. Those skilled in the art will use an appropriate apparatus if the composition is to be administered as a spray. Alternatively, the dry composition can be mixed with sterile water or with a balanced salt solution in an infusion bottle, to be delivered in the phacoemulsification procedure if desired.

In yet another alternative embodiment, a bicameral container can be used. Those having ordinary skill in the art can devise such a bicameral container. For instance, in a typical bicameral container, there may be two sections separated by a partition or a seal. One section will contain the dry composition described above and the second section will contain sterilized water. The partition (or the seal) will prevent the contents of the two sections from combining. When needed, the partition (or the seal) can be eliminated or pierced thus allowing the contents of both sections to mix to form a clear solution to be administered to the patient.

In one particular embodiment a bicameral container 100 illustrated schematically by FIG. 1 may be used. In this embodiment, the bicameral container 100 having essentially a cylindrical shape comprises first section 1 into which a quantity of lyophilized composition 2 is placed. Container 100 further comprises second section 3 into which a quantity of a carrier (i.e., in this embodiment sterilized water) 4 is placed. The two sections are separated by partition 5 which prevents lyophilized composition 2 from uncontrollably mixing with water 4. To insure that lyophilized composition 2 and water 4 are kept separate, in some embodiments, partition 5 may include a one-way valve (not shown). Any typical standard one-way valve known to those having ordinary skill in the art may be utilized for this purpose.

It is further provided that in some embodiments (not shown) the lyophilized composition 2 and water 4 may change places, i.e., the lyophilized composition 2 may be placed into the second section 3 and water 4 into the first section 1. Other features described above remain the same, i.e., the container 100 still includes partition 5.

To operate the device 100, in order to reconstitute lyophilized composition 2, a pressure may be applied to carrier 4 using moveable plunger 6. Under pressure, the valve opens thus eliminating the partition between sections 1 and 3 and allowing carrier 4 to flow from section 3 into section 1 to mix with the lyophilized composition 2. As a result a reconstituted pharmaceutical composition is obtained, to be administered to a patient.

Those having ordinary skill in the art may employ another method of breaking partition 5 if desired. Designing such alternative method of removing the partition is well within the scope of knowledge of those having ordinary skill in the art. For example, the plunger 6 can comprise a protrusion or puncture component on the partition facing surface of the plunger 6 which when directional force is applied to the plunger the protrusion or puncture component pierces the partition 5 and allows the carrier 4 to flow from the second section 3 into the first section 1. After the pharmaceutical composition has been reconstituted in a liquid form as described above, a needle or a cannula (not shown) may be attached to device 100 at point 7, and the composition may be then injected by using the device 100 (with the needle attached to it) as a syringe.

In one further embodiment, the process of lyophilization described above may be carried out directly in the device 100. To wit, a liquid composition 6 may be placed into section 1 of the device 100 prior to being lyophilized, followed by lyophilization by vacuum freeze-drying as discussed above, i.e, thereby producing lyophilized composition 2. When the process of lyophilization is thus completed, section 1 of the device 100 will have lyophilized composition 2 contained within section 1 followed by the process of reconstituting lyophilized composition 2 as described above.

The reconstituted composition can then be used for surgically treating an ophthalmological disease, condition, disorder, syndrome or pathology in a mammalian subject such a human when it is necessary to administer an active component described in the application, e.g., epinephrine, as a part of surgical treatment. In addition to humans, the reconstituted composition can be also used for treating of variety of animals, such as cats, dogs and farm animals if necessary.

Non-limiting examples of the ophthalmological disease, condition, disorder, syndrome or pathology to be treated include cataract surgery, glaucoma surgery, surgery to treat diseases of retina and prevention of floppy iris syndrome that may otherwise occur during other kinds of eye surgery. While it is envisioned that the above described compositions are primarily to be delivered to an eye of the patient by an intraocular injection, some alternative methods of delivery may be also acceptable if desired. Examples of such alternative methods include delivery via eye drops or via a spray as mentioned above. Those skilled in the art will formulate most appropriate eye drop and/or spray formulation(s) using lyophilized compositions described above, according to the best pharmaceutical practices.

The composition of the present disclosure may be used to rapidly dilate a subject's pupils. In certain embodiments, the composition may be used to dilate a subject's pupils before and/or during surgery, such as cataract surgery, glaucoma surgery, or surgery to treat diseases of retina, caract combined with microincisional glaucoma surgery (aka MIGS procedure), placement of a stent (including Hydrus, iStent, etc.), ab interno canaloplasty with OMNI, goniotomy, goniosynechialysis, and other ophthalmologic procedures where dilation of the pupil may be indicated.

In some embodiments, the size of the subject's pupil may be from about 1.0 mm to about 6.5 mm before administration of the composition of the present disclosure. In some aspects, the size of the subject's pupil before administration of the composition of the present disclosure may be from about 1.0 mm to about 1.5 mm, about 1.5 mm to about 2.0 mm, about 2.0 mm to about 2.5 mm, about 2.5 mm to about 3.0 mm, about 3.0 mm to about 3.5 mm, about 3.5 mm to about 4.0 mm, about 4.0 mm to about 4.5 mm, about 4.5 mm to about 5.0 mm, about 5.0 mm to about 5.5 mm, about 5.5 mm to about 6.0 mm, or about 6.0 mm to about 6.5 mm. In some additional aspects, the size of the subject's pupil before administration of the composition of the present disclosure may be about 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.2 mm, 2.4 mm, 2.6 mm, 2.8 mm, 3.0 mm, 3.5 mm, 4.0 mm, 4.5 mm, 5.0 mm, 5.5 mm, 6.0 mm, or about 6.5 mm.

In some additional embodiments, the size of the subject's pupil may be from about 6.0 mm to about 8.0 mm after administration of the composition of the present disclosure. In some aspects, the size of the subject's pupil after administration of the composition of the present disclosure may be from about 6.0 mm to about 6.5 mm, about 6.5 mm to about 7.0 mm, about 7.0 mm to about 7.5 mm, or about 7.5 mm to about 8.0 mm. In some additional aspects, the size of the subject's pupil after administration of the composition of the present disclosure may be about 6.0 mm, 6.1 mm, 6.2 mm, 6.3 mm, 6.4 mm, 6.5 mm, 6.6 mm, 6.7 mm, 6.8 mm, 6.9 mm, 7.0 mm, 7.1 mm, 7.2 mm, 7.3 mm, 7.4 mm, 7.5 mm, 7.6 mm, 7.7 mm, 7.8 mm, 7.9 mm, or about 8.0 mm.

In some embodiments, the change in size of a subject's pupil after administration of the composition of the present disclosure may be between about 2.0 mm to about 7.0 mm. In some aspects, the change in size of a subject's pupil may be between about 2.0 mm to about 4.0 mm, about 3.0 mm to about 5.0 mm, about 4.0 mm to about 6.0 mm, about 5.0 mm to about 7.0 mm, about 3.0 mm to about 6.0 mm, or about 4.0 mm to about 5.0 mm. In some additional aspects, the change in size of a subject's pupil may be between about 2.0 mm to about 2.5 mm, 2.5 mm to about 3.0 mm, about 3.0 mm to about 3.5 mm, about 3.5 mm to about 4.0 mm, about 4.0 mm to about 4.5 mm, about 4.5 mm to about 5.0 mm, about 5.0 mm to about 5.5 mm, about 5.5 mm to about 6.0 mm, about 6.0 mm to about 6.5 mm, or about 6.5 mm to about 7.0 mm. In still additional aspects, the change in size of a subject's pupil after administration of the composition of the present disclosure may be about 2.0 mm, 2.5 mm, 3.0 mm, 3.5 mm, 4.0 mm, 4.5 mm, 5.0 mm, 5.5 mm, 6.0 mm, 6.5 mm, or about 7.0 mm.

In some embodiments, a composition of the present disclosure may be administered to dilate a subject's pupils. In some aspects, the dilation may occur in less than one minute. In some additional aspects, the dilation may occur within between about 10 seconds and about 40 seconds, about 15 to about 35 seconds, or about 20 seconds to about 30 seconds. In yet additional aspects, the dilation may occur within about 10 seconds to about 15 seconds, about 15 seconds to about 20 seconds, about 20 seconds to about 25 seconds, about 25 seconds to about 30 seconds, about 30 seconds to about 35 seconds, or about 35 seconds to about 40 seconds. In still additional aspects, the dilation may occur within about 10 seconds, 15 seconds, 20 seconds, 25 seconds, 30 seconds, 35 seconds, or about 40 seconds.

It will be understood by those having ordinary skill in the art that the specific dose level and frequency of dosage for any particular patient may be varied and will depend upon a variety of factors including the activity of the specific compound employed, the metabolic stability and length of action of that compound, the age, body weight, general health, gender, diet, and the severity of the particular ophthalmological condition being treated.

In additional embodiments, pharmaceutical kits are provided. The kit includes a sealed container approved for the storage of pharmaceutical compositions, the container containing one of the above-described pharmaceutical compositions. An instruction for the use of the composition and the information about the composition are to be included in the kit.

The following examples are provided to further elucidate the advantages and features of the present application, but are not intended to limit the scope of the application. The examples are for the illustrative purposes only. USP pharmaceutical grade products were used in preparing the formulations described below.

Example 1

Preparing a Pharmaceutical Composition

A pharmaceutical composition was prepared as described below. The following products were used in the amounts and concentrations specified, sufficient to prepare 100 vials of 1:1,000 lyophilized injections (1 mg/mL): 1.2 mg per vial.

(1) about 0.120 g of DL-epinephrine HCl hydrochloride;

(2) about 0.80 g of sodium chloride;

(3) about 0.01 g of edetate disodium;

(4) about 0.01 g of acetylcysteine;

(5) hydrochloric acid/sodium hydroxide, for pH adjustment; and (6) about 100 ml of sterile water for injection, quantum sufficiat.

Components shown above were protected from light and air to minimize oxidation and degradation. Half the volume of sterile water for injection was added to a depyrogenated glass vessel followed by components (1)-(4) in the quantities shown above. Sufficient quantity of sterile water for injection was then added to obtain a required volume. So combined products were then mixed until completely dissolved and a clear solution was obtained. pH of the solution was adjusted to about 6.0 with hydrochloric acid and/or sodium hydroxide. Further processing described below was completed in a clean room.

The solution obtained as described above was filtered through 0.22 micron Supor filters into depyrogenated, sterilized (by autoclaving) vials, partially capped with three prong lyophilization stoppers and immediately frozen at about −71° C. for about 24 hours to allow complete freezing and proper ice crystal formation. Degassing of solution prior to freeze-drying is optional but not necessary in this method.

Frozen vials were then placed into vacuum chamber, vacuum drawn and freeze drying process commenced. Two stage drying process (primary and secondary drying) over the next 24 hours took place during this time. When completed, vials were fully stoppered and sealed. Powder cake present inside vial was completely dry, stable and both sulfite free and preservative free.

The final product was tested chromatographically (HPLC) for potency and stability after being stored for some time. After about 5 weeks and again after about 4 months it remained stable and has retained its potency. No visually perceptible change of color has been observed.

Example 2

Re-Constituting a Lyophilized Pharmaceutical Composition

The composition prepared as described in Example 1 was then re-constituted about 30 minutes prior to being administered to a patient. A quantity of sterile water for injection was added to the dry composition prepared as described in Example 1 in a vial and a clear solution was obtained. The final product ready for injection contained about 1 mg/mL of epinephrine, i.e., was a 1:1,000 aqueous solution.

Example 3

Pharmaceutical Composition

A pharmaceutical composition of the present disclosure was prepared as described below:

(1) about 0.05 g tropicamide
(2) about 1 g phenylephrine hydrochloride
(3) about 1 g lidocaine hydrochloride
(4) about 0.05 g diclofenac sodium
(5) about 0.1 g EDTA disodium
(6) about 0.185 g sodium chloride
(7) about 0.352 g boric acid
(8) about 0.1 g Polysorbate-80
(9) sodium hydroxide and/or hydrochloric acid as needed to adjust pH to 6.5±0.1
(10) sterile water for injection to bring final weight to 100 g.

A de-pyrogenated mixing vessel was obtained and calibrated to the required final volume. Sterile water for injection was added to approximately 80% of the final volume with a spin bar. The vessel was placed on a heating plate under a Ross Mixer and started mixing at 3000±500 RPM. The sterile water for injection was then heated up to 60° C.

While maintaining a temperature of 55-60° C., tropicamide was added to the vessel slowly to avoid clumping. The solution was allowed to mix for at least 30-40 minutes to allow the tropicamide to dissolve. Once the solution was clear, the heat was turned off and the solution was allowed to cool to room temperature before other ingredients were added.

Next, the sodium chloride, EDTA, boric acid, phenylephrine hydrochloride, lidocaine, and Polysorbate-80, and diclofenac were added sequentially. Each ingredient was allowed to dissolve completely before the next was added. Once the diclofenac was completely dissolved, the pH of the solution was checked while mixing. The target pH was 6.5±0.1. If the pH was not within the target range, sodium hydroxide and/or hydrochloric acid was added dropwise to adjust to the target range.

Once the pH was in the target range, sterile water for injection was added to bring the solution to its final volume. The solution was then filtered through a 0.22 micron filter into an appropriate sterile dispensing container.

Example 4

Rapid Pupil Dilation Study 1

A composition of the present disclosure was prepared as described in Example 3 and administered to 15 patients. The pupil size of the patient was measured before administration of the composition. Then, once the composition was administered, the time required for the pupil to dilate was measured and recorded. The final pupil size was measured and recorded. The results are reported in Table 1 below.

TABLE 1

| Case # | Pupil Sz 1 (mm) | Time to Dilate (min) | Pupil Sz 2 (mm) | Pupil Sz Final (mm) |
|---|---|---|---|---|
| 1 | 1.9 | 0.30 | 6.5 | 8.0 |
| 2 | 1.8 | 0.45 | 6.8 | 8.0 |
| 3 | 6.0 | 0.35 | 8.0 | 8.0 |
| 4 | 6.2 | 0.45 | 7.0 | 7.0 |
| 5 | 2.0 | 0.30 | 7.0 | 7.0 |

TABLE 1-continued

| Case # | Pupil Sz 1 (mm) | Time to Dilate (min) | Pupil Sz 2 (mm) | Pupil Sz Final (mm) |
|---|---|---|---|---|
| 6 | 8.0 | 0.30 | 8.0 | 8.0 |
| 7 | 2.0 | 0.30 | 7.0 | 8.0 |
| 8 | 1.8 | 0.42 | 6.0 | 8.0 |
| 9 | 1.8 | 0.40 | 5.0 | NA |
| 10 | 1.5 | 0.51 | 6.0 | 6.5 |
| 11 | 1.5 | 0.30 | 6.0 | 7.0 |
| 12 | 2.0 | 0.35 | 6.0 | 7.0 |
| 13 | 2.5 | 0.35 | 6.5 | 8.0 |
| 14 | 1.5 | 0.40 | 6.0 | 6.0 |

Example 5

Rapid Eye Dilation Study 2

A study was conducted to compare the effects of administration of the composition of the present disclosure with a comparator mydriatic composition. The study was conducted in 42 human patients undergoing cataract surgery with or without a MIGS procedure. Patients were given a compounded intracameral injection comprising 0.02% tropicamide, 0.3% phenylephrine HCl, 1.0% lidocaine, and 0.01% diclofenac (the "disclosed composition") in one eye. In the other eye, the patient received an injection containing lidocaine and phenylephrine (the "comparator composition"). Pupil size was measured prior to injection, 10-30 seconds after injection, and just before insertion of the intraocular lens (IOL).

Figure 2:
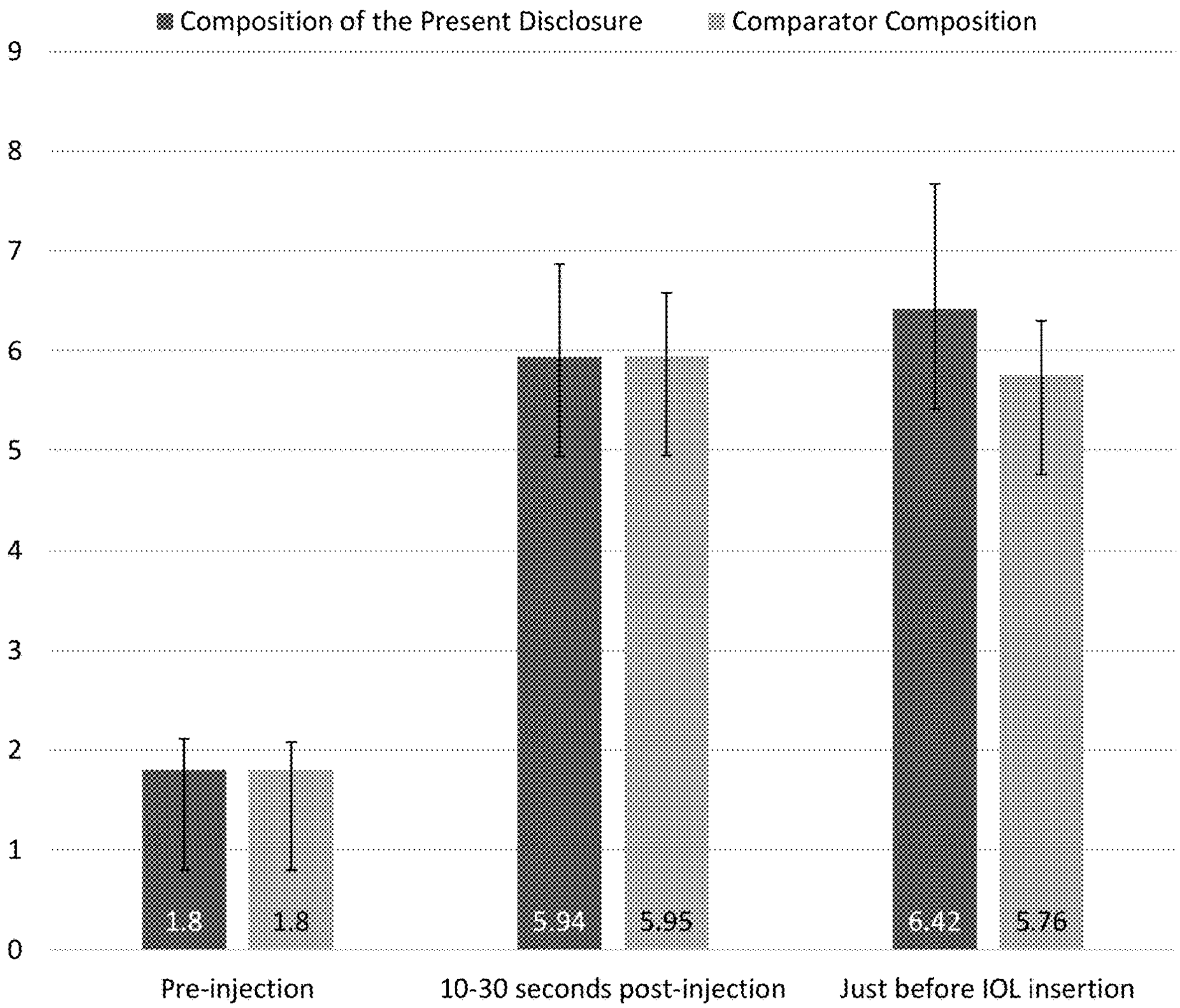
FIG. 2 is a graph comparing the pupil diameter and stability of dilation for patients receiving an injection of the composition of the present disclosure compared to patients receiving an injection of a comparator composition.
Figure 3:
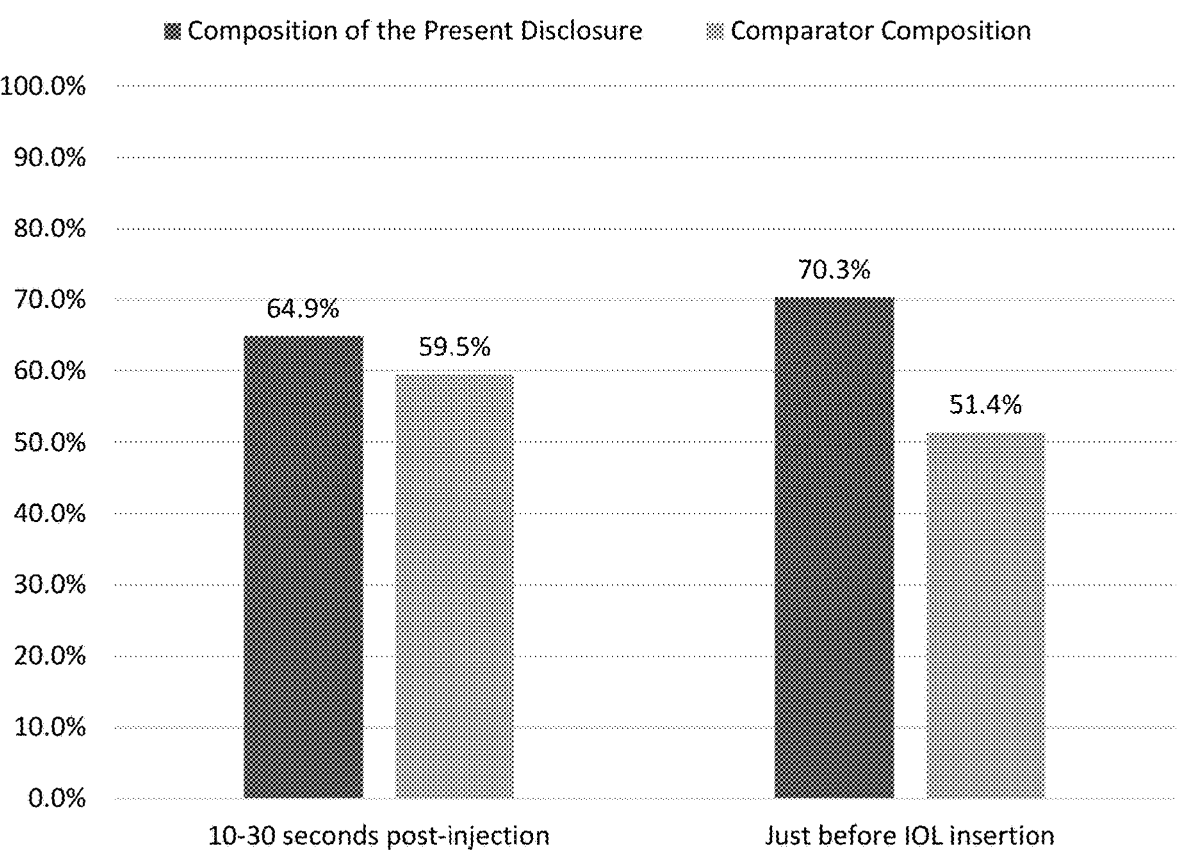
FIG. 3 is a graph comparing the percentage of patients receiving an injection of a composition of the present disclosure and a comparator composition who had pupil diameters greater than 6.0 mm at 10-30 seconds after injection and just before IOL insertion.

Results of the study are shown in FIGS. 2 and 3. FIG. 2 shows that the mean pupil diameter pre-injection was about 1.8 mm for both patients receiving the disclosed composition and the comparator composition. Ten to thirty seconds after injection, the mean pupil diameter was 5.94 mm for patients receiving the disclosed composition and about 5.95 for patients receiving the comparator composition. Before IOL insertion, mean pupil size was 6.42 mm for patients receiving the disclosed composition and about 5.76 mm for patients receiving the comparator composition. Therefore, the study shows that the disclosed composition achieved longer-lasting pupil dilation than the comparator composition.

FIG. 3 shows the number of patients that achieved a pupil diameter of greater than or equal to 6.0 mm after injection of the disclosed composition and after injection of the comparator composition. Ten to thirty seconds after injection, 64.9% of patients receiving the disclosed composition achieved pupil dilation of greater than or equal to 6.0 mm, while only 59.5% of patients receiving the comparator composition achieved pupil dilation of greater than or equal to 6.0 mm. Before IOL insertion, 70.3% of patients receiving the disclosed composition achieved pupil dilation of greater than or equal to 6.0 mm, while only 51.4% of patients receiving the comparator composition achieved pupil dilation of greater than 6.0 mm. These results show that patients receiving the disclosed composition not only achieved longer-lasting pupil dilation compared to those receiving the comparator composition, but that their pupil size was larger overall. Surprisingly, some patients receiving the comparator composition showed a reduction in pupil size between the period 10-30 seconds post-injection and just before IOL insertion.

It is also of note that one patient in the study required use of a pupil expander after receiving the comparator composition due to poor pupil dilation. The same patient received the disclosed composition in the other pupil and showed stable pupil dilation.

Although the invention has been described with reference to the above examples, it will be understood that modifications and variations are encompassed within the spirit and scope of the invention. Accordingly, the invention is limited only by the following claims.

What is claimed is:

1. A method of rapidly dilating a subject's pupils, the method comprising:

administering to the subject via intraocular injection a therapeutically effective amount of a composition consisting of:

a therapeutically effective quantity of phenylephrine hydrochloride;

a therapeutically effective quantity of tropicamide having a concentration in the composition of about 0.04% (w/v) to about 0.06% (w/v);

at least one metal chelator;

at least one anesthetic;

optionally, at least one tonicity adjusting agent comprising one or more chloride salts selected from the group consisting of sodium chloride, potassium chloride, and magnesium chloride;

optionally, hydrochloric acid and/or sodium hydroxide;

at least one non-steroid anti-inflammatory drug;

optionally, at least one excipient; and a quantity of sterile water, wherein the subject's pupils are dilated from a first diameter to a second diameter within one minute or less after administering the composition, wherein the difference between the first diameter and the second diameter is from about 5.0 mm to about 7.0 mm.

2. The method of claim 1 wherein the subject's pupils have a diameter of at least about 1.0 mm before administration of the composition.

3. The method of claim 1 wherein the subject's pupils have a diameter of at least about 6.0 mm after administration of the composition.

4. The method of claim 1 wherein the subject's pupils are dilated within 40 seconds or less after administering the composition.

5. The method of claim 4 wherein the subject's pupils are dilated within 30 seconds or less after administering the composition.

6. The method of claim 1, wherein the at least one metal chelator is ethylenediaminetetraacetic acid or a pharmaceutically acceptable salt thereof.

7. The method of claim 1, wherein the at least one non-steroid anti-inflammatory drug is diclofenac.

8. The method of claim 1, wherein the at least one anesthetic is lidocaine.

9. The method of claim 1, wherein the at least one excipient is selected from the group consisting of boric acid and polysorbate-80.

10. The method of claim 1, wherein the phenylephrine hydrochloride has a concentration in the composition of between about 0.02% (w/v) to about 1.5% (w/v).

11. The method of claim 10, wherein the phenylephrine hydrochloride has a concentration in the composition of about 1% (w/V).

12. The method of claim 1, wherein the tropicamide has a concentration in the composition of about 0.05% (w/v).

13. The method of claim 7, wherein the diclofenac has a concentration of between about 0.04% (w/v) to about 0.5% (w/v).

14. The method of claim 13, wherein the diclofenac has a concentration in the composition of about 0.05% (w/v).

15. The method of claim 8, wherein the lidocaine has a concentration of between about 0.5% (w/v) to about 1.5% (w/V).

16. The method of claim 15, wherein the lidocaine has a concentration in the composition of about 1% (w/V).

* * * * *